United States Patent [19]

Surgi

[11] Patent Number: 5,043,285
[45] Date of Patent: Aug. 27, 1991

[54] OPTICAL DETECTION OF OXYGEN

[75] Inventor: Marion R. Surgi, Evanston, Ill.

[73] Assignee: Allied-Signal Inc., Morris Township, Morris County, N.J.

[21] Appl. No.: 71,445

[22] Filed: Jul. 9, 1987

[51] Int. Cl.$^5$ .............................................. G01N 21/64
[52] U.S. Cl. ..................................... 436/136; 436/68; 436/172; 422/82.06; 422/91; 250/458.1
[58] Field of Search ...................... 422/68, 83, 88, 91, 422/82.05, 82.06, 82.07, 82.08; 436/68, 136, 172; 128/634, 665, 666; 250/458.1, 459.1; 356/39-41

[56] References Cited

U.S. PATENT DOCUMENTS

| | | | |
|---|---|---|---|
| 3,612,866 | 10/1971 | Stevens | 250/71 |
| 3,725,658 | 4/1973 | Stanley et al. | 250/71 R |
| 3,968,051 | 7/1976 | Stamm et al. | 522/78 X |
| 4,281,294 | 7/1981 | Volkin | 372/79 X |
| 4,451,264 | 5/1984 | Ulrey et al. | 8/508 |
| 4,476,870 | 10/1984 | Peterson et al. | 128/634 |
| 4,580,059 | 4/1986 | Wolfbeis et al. | 250/459 |
| 4,657,736 | 4/1987 | Marsoner et al. | 422/56 |
| 4,775,514 | 10/1988 | Barnikol et al. | 436/136 X |
| 4,810,655 | 3/1989 | Khalil et al. | 436/136 X |
| 4,895,156 | 1/1990 | Schulze | 128/634 |

OTHER PUBLICATIONS

Lamola, "J. Chem. Phys.", 47, 4810–4816 (1967).
Merkel et al., J. Chem. Phys., 58(1), 398–400 (1973).
Lee, Eric D., "Luminescence Ratio Indicators for Oxygen," *American Chemical Society*, vol. 59, No. 2, Jan., 1987, pp. 279–283.

*Primary Examiner*—David L. Lacey
*Assistant Examiner*—Jeffrey R. Snay
*Attorney, Agent, or Firm*—Harold N. Wells; Mary Jo Ryther; Gerhard H. Fuchs

[57] ABSTRACT

This invention is a method and apparatus for detecting the presence of gaseous oxygen and measuring the amount present. In the practice of the invention, luminescence from a luminophor compound is quenched by oxygen. The luminiphor is a conjugated aromatic carbonyl. The intensity of the emitted light is related to the concentration of oxygen in the atmosphere surrounding the conjugated aromatic carbonyl compound. The luminophor compound is located on a polar substrate having free hydroxyl groups at its surface and also having at its surface, in locations adjacent to the luminophor compound, a halogenated hydrocarbon compound containing at least one halogen selected from a group consisting of chlorine, bromine, and iodine. In a preferred embodiment, the invention comprises an oxygen sensor utilizing a fiber-optic light guide to conduct excitation light to a substrate comprised of activated silica gel particles having methylene chloride and N-methylacridone co-deposited on them. A fiber-optic light guide is used to conduct emitted light away from the substrate.

17 Claims, 2 Drawing Sheets

N-methylacridone

OPTICAL DETECTION OF OXYGEN

FIELD OF THE INVENTION

This invention relates to spectroscopy.

BRIEF SUMMARY OF THE INVENTION

This invention is a method and apparatus for detecting the presence of gaseous oxygen and measuring the amount present. In the practice of the invention, luminescence, which may be defined as an emission of light, from a luminophor compound is quenched by oxygen. The luminophor is a conjugated aromatic carbonyl. The intensity of the emitted light is related to the concentration of oxygen in the atmosphere surrounding the conjugated aromatic carbonyl compound. The compound is located on a polar substrate having free hydroxyl groups at its surface and also having at its surface, in locations adjacent to the carbonyl compound, a halogenated hydrocarbon compound containing at least one halogen selected from a group consisting of chlorine, bromine, and iodine.

In a preferred embodiment, the invention comprises an oxygen sensor utilizing a fiber-optic light guide to conduct excitation light to a substrate comprised of activated silica gel particles having methylene chloride and N-methylacridone co-deposited on them. A fiber-optic light guide is used to conduct emitted light away from the substrate. It is highly likely that the luminescence is phosphorescence, but it is possible that the observed emission is a different phenomenon, such as delayed excimer fluorescence.

It is an object of the present invention to provide a method and apparatus for the optical determination of oxygen over a broad range of temperatures, including normal ambient temperatures.

It is also an object of this invention to provide a method and apparatus for oxygen determination which is reversible, so that multiple analyses can be accomplished using the same sensing element.

It is a further object of this invention to provide an oxygen sensor which is relatively small and inexpensive to manufacture.

In addition, it is an object of this invention to provide a method and apparatus to analyze oxygen in situ, that is, without withdrawing the substance which is analyzed from a containing vessel or pipeline.

In a broad embodiment, the present invention comprises means for producing substantially monochromatic excitation light; a sensing element comprised of: (1) a polar substrate having free hydroxyl groups at its surface; (2) a luminophor compound, which is a conjugated aromatic carbonyl compound, deposited on the surface of said substrate; and, (3) a halogenated hydrocarbon compound deposited on the surface of said substrate at locations adjacent to said carbonyl compound, wherein the halogenated hydrocarbon compound contains at least one halogen selected from a group consisting of chlorine, bromine, and iodine; means for exposing said sensing element to said excitation light; means for collecting light emitted by said carbonyl compound; means for filtering said collected light to remove scattered excitation light and stray light which is collected along with said emitted light; means for measuring the intensity of said filtered light; means for exposing said sensing element to a sample environment comprising gaseous oxygen; means for exposing said sensing element to calibration environments; and, means for determining oxygen concentration in said sample environment by comparing light intensity measured while the sensing element is exposed to said sample environment to light intensities measured while the sensing element is exposed to said calibration environments.

The present invention is a method for detecting the presence of gaseous oxygen and measuring the amount present comprising: exciting a luminophor compound with substantially monochromatic light having wavelengths effective for absorption by said luminophor, where the luminophor is located on a polar substrate having free hydroxyl groups, where a halogenated hydrocarbon compound containing at least one halogen selected from a group consisting of chlorine, bromine, and iodine is located on the substrate at locations adjacent to the luminophor, and where the luminophor is a conjugated aromatic carbonyl; collecting light emitted by the luminophor at wavelengths different from those of said excitation light; measuring the intensities of said collected light when said luminophor is located in a calibration environment comprising gaseous oxygen of at least two different concentrations, thus providing at least two intensity measurements; measuring the intensity of said collected light when said luminophor is located in a sample environment comprising gaseous oxygen; and, determining the oxygen concentration of said sample environment by comparing said sample environment intensity to said calibration environment intensities.

An oxygen sensor of the present invention is comprised of a polar substrate having free hydroxyl groups at its surface; a luminophor compound, which is a conjugated aromatic carbonyl compound, deposited on the surface of said substrate; a halogenated hydrocarbon compound deposited on the surface of said substrate at locations adjacent to said carbonyl compound, wherein the halogenated hydrocarbon compound contains at least one halogen selected from a group consisting of chlorine, bromine, and iodine; at least one fiber-optic light guide for conducting excitation light to said substrate; and, at least one fiber-optic light guide for conducting light emitted by said carbonyl compound away from said substrate.

INFORMATION DISCLOSURE (Marsoner et al.) U.S. Pat. No. 4,657,736 teaches a sensor element for oxygen comprising a fluorescent indicator substance incorporated into a silicone polymer. The indicator substance is chemically modified by reacting it with tertiary butyl chloride in a mutual solvent (carbon disulfide) using aluminum chloride as a catalyst. The resultant substance is washed, dried, and subjected to an evaporation step to produce an oily residue which is combined with a polymer. Alternatively, the carbon disulfide may be replaced with a large amount of tertiary butyl chloride.

(Peterson and Fitzgerald) U.S. Pat. No. 4,476,870 show a probe in which fiber optics are used in monitoring the partial pressure of oxygen by means of fluorescence quenching.

U.S. Pat. Nos. 3,612,866 (Stevens), 3,725,658 (Stanley and Kropp), and 4,580,059 (Wolfbeis and Urbano) are representative of references which show oxygen determination using fluorescence quenching of pyrene and similar compounds. In '866, column 1, line 71, it is stated that phosphorescence is rarely observed in fluid media;

it is believed that the present invention utilizes the phenomenon of phosphorescence.

An article by Lee et al. in *Analytical Chemistry* (vol. 59, no. 2, January 1987, p. 279) discusses oxygen indicator systems which have two luminescence bands.

DETAILED DESCRIPTION OF THE INVENTION

Figure 1:
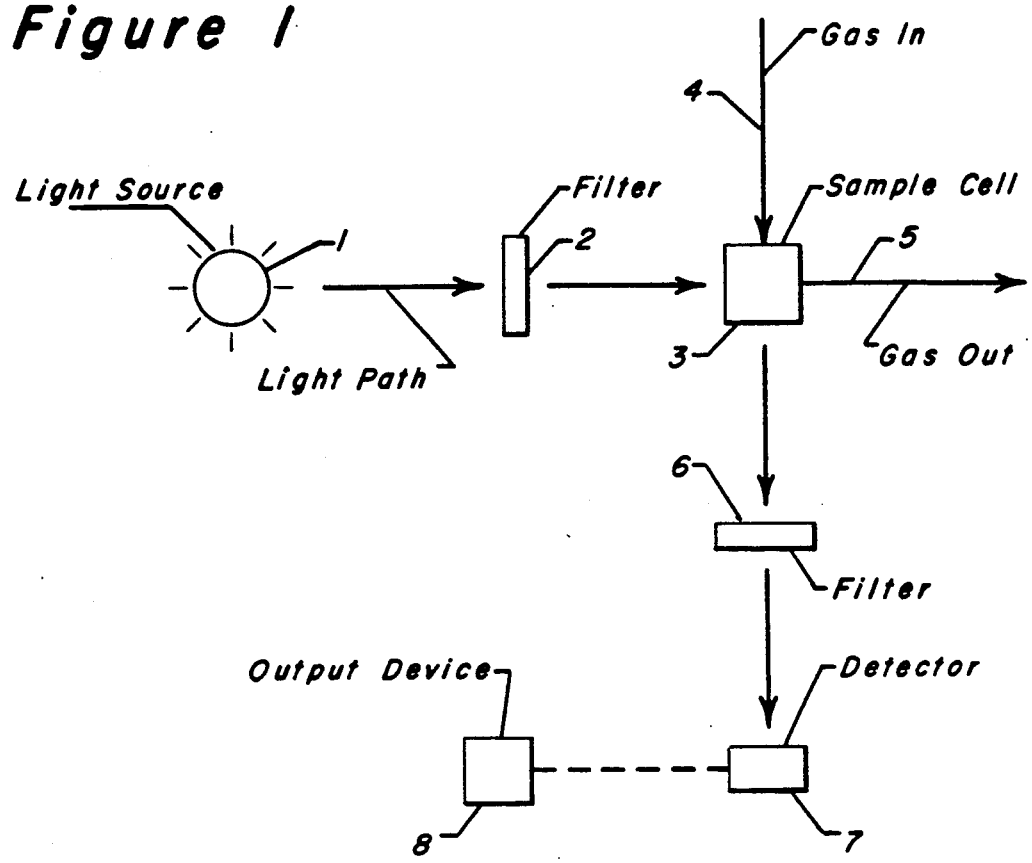
FIG. 1 is a schematic diagram depicting the major items of apparatus used in the practice of the invention.

Oxygen monitoring is of interest in many processes, such as combustion control, blood gas determination, and biofermenter control. The present invention provides method and apparatus which is useful in these applications and numerous others wherein it is desired to measure the concentration of oxygen in gases and liquids.

Certain substances, which may be termed indicator substances, are useful in connection with the phenomena of luminescence and luminescence quenching. Luminescence may be defined as an emission of light which is not ascribable directly to incandescence. A substance which emits light may also be termed a luminophor. Luminescence quenching is the diminishment of intensity of luminescence which results from the presence of a particular substance. An indicator substance of the present invention will emit light of a particular wavelength upon exposure to light of a different particular wavelength, which may be termed incident light or excitation light. Incident light is absorbed by molecules of the indicator substance, thereby causing them to move from a ground state to a state of higher energy known as an excited state. In order to return to the ground state, energy in the form of light or heat is emitted. The amount of time that any one molecule remains in the excited state is very short, much less than one second. Emitted light must be distinguished from reflected light, also termed scattered light, which is incident light "bouncing off" the indicator substance.

In the present invention, an indicator substance, in conjunction with other substances necessary to the practice of the invention, is exposed to excitation light when the indicator substance is located in a sample environment comprised of oxygen and also when the indicator substance is located in calibration environments having known concentrations of oxygen. The intensity of the light emitted by the indicator substance is diminished by the presence of oxygen and the magnitude of the loss in intensity is related to the amount of oxygen present.

In a form of luminescence known as fluorescence, absorption of incident light causes a fluorescent substance to assume a state of higher energy termed the excited singlet state. The substance is unstable in this state and returns to its ground state by emitting heat or light of a characteristic wavelength, the emission of light being fluorescence.

In a form of luminescence known as phosphorescence, a substance assumes the excited singlet state and then assumes the triplet state. Light emitted at a characteristic wavelength upon returning to the ground state from the triplet state is termed phosphorescence. Characteristics of phosphorescence which make it an attractive phenomenon for use in sensing oxygen include its relatively long lifetime and a significant wavelength separation between excitation light and emitted light. It is believed that the light emitted by the indicator substances of the present invention is phosphorescence. However, there is a possibility that the observed emission is delayed excimer (excited state dimer) fluorescence quenching. However, that the mechanism is not yet certain is not relevant to the practice of the invention, since the invention is effective in measuring oxygen concentration.

Figure 3:
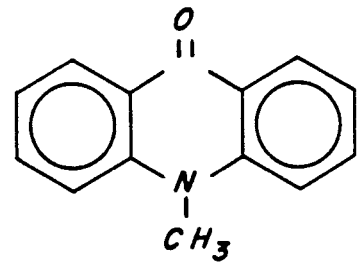
FIG. 3 shows the chemical structure of the preferred luminophor.

The indicator substance used in the practice of the present invention was N-methylacridone (NMA), which is a conjugated aromatic carbonyl. FIG. 3 shows the structure of an NMA molecule. It is believed that other conjugated aromatic carbonyls, which are also termed aromatic ketones, will be effective as indicator substances. Examples of such conjugated aromatic carbonyls include bioanthrone, acridone, benzophenone, and fluorenone.

The indicator substance, or luminophor, must be located on a substrate which is polar and has free hydroxyl groups at its surface. Activated silica gel particles were used in experimentation related to the present invention. Other materials which will serve as substrates are alpha alumina, acidic ion-exchange resins, and glass which has been etched with a strong acid. A brief experiment with alpha alumina was conducted but terminated when water in the sample gas affected the alumina substrate. However, it is believed that alpha alumina will serve as an effective substrate if water is removed from the gases in contact with it. Spherical particles or beads are a preferred physical form for the substrate, but other physical forms may be used; for example, excitation light may be directed to a flat substrate.

It is necessary to the practice of the invention that a halogenated hydrocarbon be located on the substrate adjacent to the luminophor. Methylene chloride was utilized, but it is believed that other halogenated hydrocarbons having up to about three carbon atoms will be equally satisfactory. Examples of such halogenated hydrocarbons are dichloromethane, diiodomethane, methyl iodide, 1-bromo-2-chloroethane, 1-bromo-1-chloroethane, iodoform, 1,1-dibromoethane, and methylene chloride.

It is believed that a heavy atom is needed in the system comprised of the substrate and the carbonyl; the heavy atom is the halogen and use of a halogenated hydrocarbon solvent is simply a convenient method of providing the heavy atom as well as providing a method of depositing the NMA on the substrate. In the fabrication of a sensing element, much of the solvent is evaporated, but a sufficient amount of heavy atoms are left on the substrate surface. Use of a solvent with a high molecular weight, that is, more than three or four carbon atoms, would result in difficulties in evaporating the solvent.

It is believed that determination of oxygen by the present invention is made possible by the interactions among the three components discussed above. The surface of silica gel consists of siloxane bridges between tetravalent silicon atoms and isolated silanol groups. Activation of the silica increases the number of silanol groups, that is, the number of hydroxyl ions attached to silicon atoms at the surface. Polar hydrogen bonds are formed between the carbonyl and silanol groups. In this manner, the interaction between the substrate and the luminophor increases the population of the triplet state, thus increasing the amount of light emitted as luminophor molecules return to the ground state.

Intersystem crossing, that is, the transition from the excited singlet state to the triplet state is also facilitated by the presence of heavy atoms in physical contact with the carbonyl molecules, by means of a mechanism known as spin orbit coupling. Thus, the intensity of light emitted from the luminophor is further increased.

In summary, it is believed that combining the two effects which occur when heavy atoms contained in halogenated hydrocarbons and when a polar substance having free hydroxyl groups are both brought into contact with a conjugated aromatic carbonyl substantially increases the population of the triplet state, thus enhancing the emission of light called phosphorescence, where the emission is sufficiently long-lived and of such a magnitude that the phenomenon can be easily observed and used.

FIG. 1 depicts basic elements which may be used in the practice of the present invention in block diagram form. Light from a source 1, which may be a xenon arc lamp or a tungsten filament lamp, is passed through optical cutoff filter 2, which allows only light having wavelengths of around about 400 nanometers (nm) to pass through it. A monochromator may be used in place of the optical filter. Light of other wavelengths is blocked by the filter. Substantially monochromatic light, having wavelengths centered about 400 nm and ranging from about 395 to about 405 nm, is provided to sample cell 3. An oxygen sensing element located inside of sample cell 3 is exposed to the monochromatic light, which may be termed excitation light. The sample cell is transparent to excitation light and also to emitted light. The sensing element is located in a gaseous environment, where the gas is provided to the sample cell by tubing 4 and flows away from the sample cell by means of tubing 5.

Light emitted from the sensing element in sample cell 3 is passed through optical cutoff filter 6, which passes only light having wavelengths centered on about 460 nm. A monochromator may be used in place of the filter. Filter 6 blocks light of wavelengths which are below about 455 nm and above 465 nm. The intensity of the light passing through filter 6 is measured by detector 7. An output device 8 receives intensity information from detector 7. The output device may simply display the intensity of the measured light or may be used to perform comparisons and determine oxygen concentrations, as will be explained below.

Figure 2:
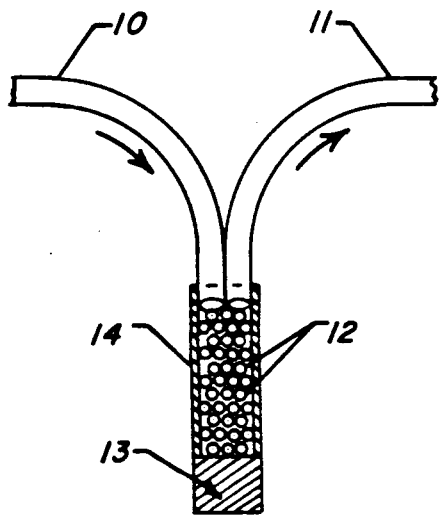
FIG. 2 is a schematic diagram of an oxygen sensor.

FIG. 2 depicts a preferred sensor. Particles of coated silica gel 12 are located within gas permeable membrane 14, which is cylindrical in form. Nonpermeable plug 13 closes one end of the cylinder formed of the membrane. Fiber-optic light guides 10 and 11 fill the other end of cylinder. Fiber-optic light guide 10 conducts light to the sensing element which is comprised of the coated particles and fiber-optic light guide 11 transmits light away from the coated particles 12. The purpose of the membrane is to contain the silica particles and to position them relative to the fiber-optic light guides.

The membrane must be permeable to the sample environment in which the concentration of oxygen is to be measured. The rate of oxygen diffusion through the membrane may initially limit the magnitude of the quenching effect and govern the transient performance of the sensor. When the environment inside the membrane becomes the same as that outside the membrane, that is, when diffusional equilibrium is reached, the magnitude of the quenching effect depends on the rate of collision between oxygen molecules and NMA molecules.

A selectively permeable membrane may be used to prevent an interfering substance in the sample environment from contacting the luminophor. By interfering substance is meant a substance which would prevent accurate measurement of oxygen concentration and/or damage the sensing element.

As used herein, the term sensor refers to apparatus which responds to a physical stimulus and transmits a signal indicative of the stimulus. As used herein a sensing element is apparatus which responds to a physical stimulus. Applying these definitions to the present invention, it can be seen that the apparatus depicted in FIG. 2 may be termed both a sensor and a sensing element and that the FIG. 2 apparatus without the fiber-optic light guides is a sensing element, but cannot be termed a sensor.

Preferred sensors of the present invention were prepared by the following typical procedure. Silica gel having a mean particle diameter of about 75 microns was washed with the following materials, in sequence: hexane, methylene chloride, ethanol, acetone, and 0.5M nitric acid. The silica gel was then activated by placing it in an air purged furnace maintained at 400° C. for 24 hours. The silica gel was purchased from Baker and had a BET surface area of 648 $m^2/g$.

A luminophor and a halogenated hydrocarbon were deposited on the activated silica gel particles by adding three mL of a solution consisting of 6450 microgram of NMA in 100 mL of methylene chloride to a VOA vial containing 0.3580 g of activated silica. The liquid methylene chloride was allowed to evaporate, under a dry nitrogen atmosphere, while the vial was rotated to ensure uniform coverage of the surface of the silica. The NMA was purchased from Aldrich Chemical Company and the methylene chloride was spectroscopic grade purchased from Burdick and Jackson; both were used without further treatment.

The fiber-optic light guides used in the preferred sensor each consisted of a single fiber and were obtained from Poly-Optical products of Santa Ana, Calif. (POM-1440 monofiber, optical grade). The core of the fiber consists of polymethylmethacrylate having a diameter of 0.98 mm, while the cladding is FEP.

In fabricating the preferred sensors, the unclad ends of two fibers were placed into an elliptical stainless steel tube and gentle heat from a soldering iron was applied until the two fibers were fused together. The fibers were cut with a hot razor and the ends were heat polished to minimize spherical aberrations.

The fused ends of the optical fibers were placed inside an end portion of a length of heat-shrinkable FEP tubing. Gentle heat was applied to the tubing, which was purchased from Cole-Parmer, to fasten the tubing to the optical fibers by means of the resultant reduction in diameter of the tubing. Wall thickness of the tubing was 0.30 mm and increased to 0.50 mm upon application of heat.

Particles of silica gel having a luminophor compound and a halogenated hydrocarbon compound co-deposited on their surface as described above were placed within the tubing adjacent to the ends of the fibers. To complete fabrication of the sensor, the open end of the tubing was plugged with an inert material. The length of tubing which was filled with particles was about 5 mm. Commercial sensors will utilize lengths of from about 2 mm to about 20 mm.

The sensor was placed in a sample cell having gas-tight fittings through which the two fiber optics extended outside of the cell. Gas from oxygen and nitrogen cylinders was passed through calcium sulfate to remove water and then through molecular sieve material to remove impurities before it was passed through the sample cell. The concentration of oxygen in nitrogen was set at desired values (from 0 to 100% oxygen) by adjusting flowmeters (rotameters) through which the two gases passed.

The light source used in the experiments was a Xenon arc lamp operated at 133 watts. A monochromator (Oriel model 77250, f/3.7 optics, with model 77269 input and output fixed slits having an aperture of 3.16 mm, 20 nm bandpass) was used to obtain substantially monochromatic excitation light. Light from the excitation monochromator was passed through a collimating lens (Oriel model 4134, f/2 optics) and then through a second lens (Oriel model 4133, f/1.5 optics) to focus the light onto the optical fiber. If an optical filter is used to replace the monochromator, the collimating lens is not required. Physical connection of the fiber to the lens was accomplished by means of a fitting which mates to the lens and has a light-tight opening through which the end portion of the fiber passes.

Emitted light carried away from the sensing element by the optical fiber was passed through a focusing lens (Oriel model 4134, 19 mm focal length, 25.4 mm diameter) and an iris, which was positioned immediately behind the lens and had a 2 mm aperture, and then into an emission monochromator. The emission monochromator was identical to the excitation monochromator except that the emission slits had an aperture of 2.0 mm. The emission monochromator was used in a scanning mode in order to investigate emissions in a wavelength range of 300 to 600 nm. Use of the iris reduced the amount of stray light entering the emission monochromator. An EMI photomultiplier measured the intensity of the emitted light at the monochromator exit slit and provided an input signal to an ammeter and chart recorder.

In a more sophisticated experimental equipment arrangement, the emission monochromator was replaced with an ISA Model HR 320 spectograph. A Princeton Applied Research Model 1420 intensifier was used to convert light from the spectograph to an output signal which was provided to a PAR Model 1460 detector-controller/optical multichannel analyzer.

An inexpensive commercial oxygen concentration instrument may use optical filters rather than monochromators and/or a spectograph, in order to minimize cost. Also, for the same reason, an inexpensive detector may be used. A United Technologies Model 10DP-195I pin diode detector was evaluated and found to be satisfactory. This photodiode detector exhibited linear response to light intensities ranging from 0.01 to 20 microwatts/cm$^2$ and provided an output current ranging from 3 to 7200 nanoamps, without the need for voltage biasing.

Figure 4:
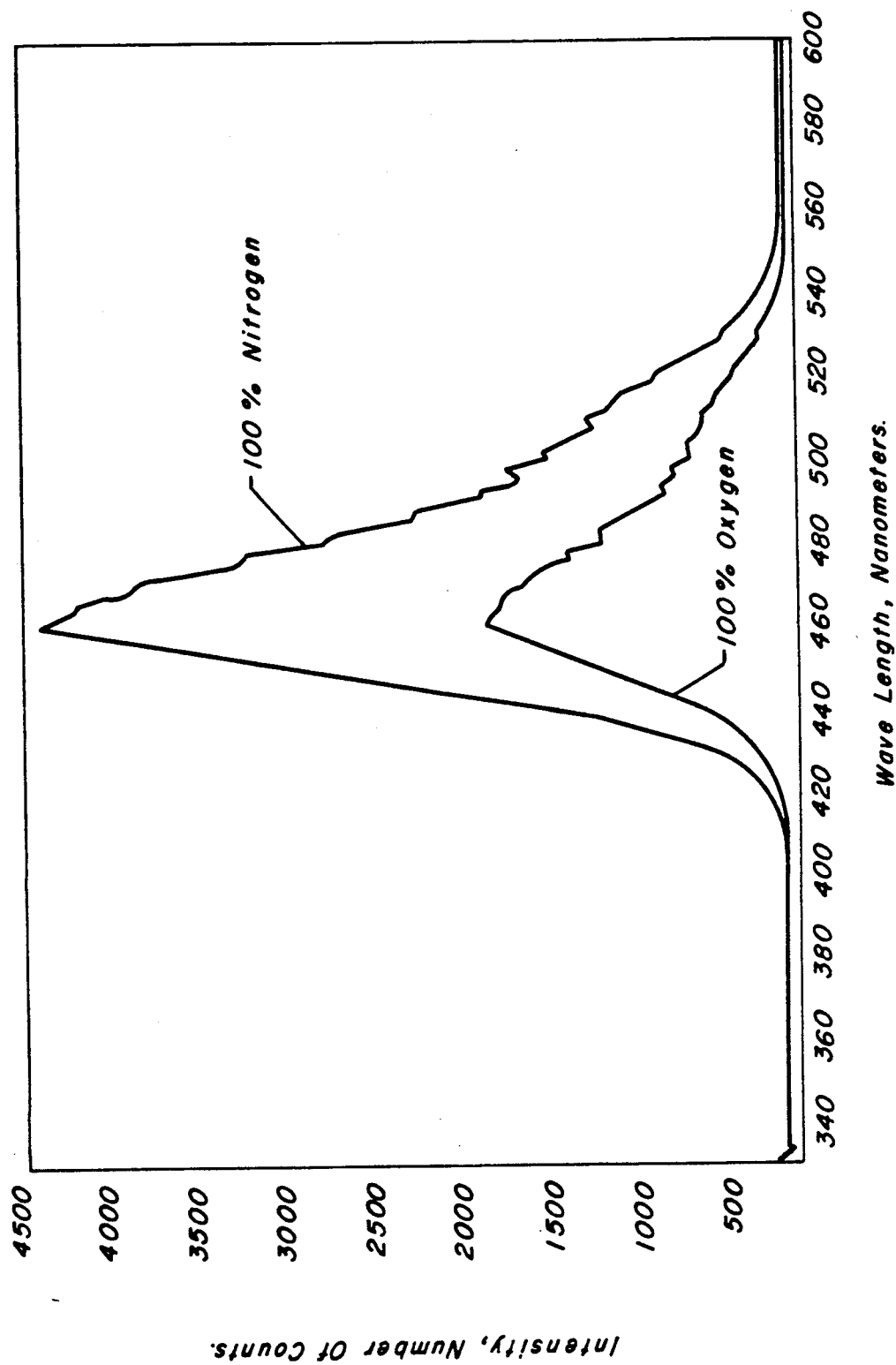
FIG. 4 is a representation of two spectrums, one recorded when a sensor of the present invention was exposed to a nitrogen environment and the other when the sensor was exposed to a pure oxygen environment.

FIG. 4 is a representation of two spectra, one recorded when a sensor was exposed to pure nitrogen and one recorded when the sensor environment was 100% oxygen. When the sensor is exposed to an oxygen concentration between 0 and 100% oxygen, the resulting spectrum will be between the two spectra of FIG. 4. The height of the sample spectrum peak at 460 nm or the area under the curve of the sample spectrum depends on the amount of oxygen present. The emitted light intensity information from the PAR Model 460 detector was provided in units of counts, as can be seen in FIG. 4.

Experimentation was conducted to determine the effects of omitting components of a sensing element. In one experiment, a compound having key similarities to NMA was substituted for NMA. This compound is 10,10'-dimethyl-9,9'-biacridylidene (DBA). Substitution of DBA for NMA illustrated the importance of the carbonyl component of NMA. In a second experiment, a sulfonated polystyrene (fluorosil) was substituted for the silica gel, in order to show the importance of a polar substrate. The substrate was omitted in a third experiment, with only NMA and methylene chloride used as a sensing element. In order to interrupt the interaction between NMA and the substrate, in a fourth experiment, methylene blue was added to the methylene chloride to coat the silica with methylene blue. In each experiment, the sensing element was ineffective for the purpose of determining oxygen concentration.

Data from a typical experiment using a sensor fabricated in the manner discussed above is presented in the Table. The intensity ratio was provided by the equipment discussed above. The actual oxygen concentrations were determined by the flowmeters used to regulate flow of oxygen and nitrogen into the sample cell.

TABLE

| $N_2$ Intensity | Oxygen Concentration, % | |
| $O_2$ Intensity | Actual | Calculated |
| --- | --- | --- |
| 1.00 | 0 | 2.2 |
| 1.33 | 8.9 | 8.0 |
| 1.54 | 15.0 | 15.0 |
| 1.89 | 27.2 | 27.0 |
| 2.05 | 33.4 | 33.4 |
| 2.31 | 46.0 | 44.2 |
| 2.50 | 59 | 53 |
| 2.70 | 65 | 63 |
| 2.90 | 79 | 75 |
| 3.03 | 86 | 84 |
| 3.18 | 100 | 97 |

The calculated oxygen concentrations are derived from the intensity ratio data by means of an equation derived from all of the data using a curve-fitting technique. The equation is as follows:

$$a\,(\%\ O_2)^2 + b\,(\%\ O_2) + c = N_2\ \text{Intensity}/O_2\ \text{Intensity}$$

where:
$a = -1.17 \times 10^{-4}$
$b = 0.0330$
$c = 1.04$

The coefficient of the squared term (a) is much smaller than that of the first order term (b), indicating that the first order term is much more significant, i.e., the relationship between oxygen concentration and the magnitude of quenching is close to linear. There is no reasonable photochemical explanation, at this time, for the nonlinearity of the sensor response; it is expected that the response will be linear if perfect measuring apparatus were available.

The response time of a sensor was measured by exposing the sensor alternately to 100% nitrogen and 100% oxygen. When switching from nitrogen to oxygen, the average response time was 12 seconds. When switching from oxygen to nitrogen, the average response time was 42 seconds. Average response time is defined as 90% of the total intensity change.

The effect of silica particle size was investigated. It was determined that use of particles having a mean diameter of about 20 microns resulted in a high level of intensity of the emitted light when quenched by oxygen. Theoretically, intensity should be independent of particle size. However, there are light coupling losses, which occur at the fiber-optic/silica interface. Large particles do not couple well and small particles block light from reaching the receiving end of the fiber-optic light guide. It was found that use of a standard commercially available size of silica, 75 microns, resulted in acceptable levels of intensity. The instant invention, then, contemplates a mean particle diameter in the range of from about 10 to about 100 microns.

The amount of luminophor used, with respect to the substrate, may be widely varied. In a series of experiments, NMA loading was varied from 150 to 1300 micrograms of NMA per gram of silica gel. The corresponding surface area of the silica which was covered by NMA varied from 0.12% to 0.55%, using BET nitrogen absorption techniques. The surface area of the 75 micron silica which was used as the substrate was 648 $m^2/g$. The emission intensity (at 460 nm) increased as NMA loading was increased up to about 540 micrograms/g, then decreased as loading was increased to about 850 micrograms/g. Above 850, intensity was independent of NMA loading.

In commercially available apparatus using the present invention, calibration data for each sensor will be collected before the sensor is placed into service. This data will consist of a measurement of quenching magnitude for each of a number of oxygen concentrations within the range to be measured by that particular sensor and will establish the calibration curve for that particular sensor and its associated apparatus. Also, it is required practice in measuring concentration to periodically calibrate the measuring apparatus by use of samples whose composition is known. That the calibration curve for each sensor is still valid will be checked by periodically running one or two known samples. Thus, it can be seen that exact adherence to theoretical relationships is not required of commercially used methods and apparatus. The primary commercial requirement is repeatability.

A sample environment refers to a substance which may contain gaseous oxygen, where it is desired to determine the concentration of oxygen in the substance. A calibration environment refers to a substance having a known concentration of oxygen.

When luminophors other than NMA are used, it may be desirable to use excitation light having a wavelength different from 400 nm, since other luminophors may absorb light of another wavelength more efficiently.

It is expected that the present invention may be used with sample environments having a broad range of temperatures. The limiting factor on the high end will be the decomposition temperature of NMA, which is above 300° C. The lowest temperature at which the present invention will be useful is expected to be about 77° K.

What is claimed is:

1. Apparatus for detecting the presence of gaseous oxygen and measuring the amount present, comprising:
   a) means for producing substantially monochromatic excitation light;
   b) a sensing element comprised of:
      (1) a polar substrate having free hydroxyl groups at its surface;
      (2) a luminophor compound, which is a conjugated aromatic carbonyl compound, deposited on the surface of said substrate wherein said luminophore compound is N-methylacridone; and,
      (3) a halogenated hydrocarbon compound deposited on the surface of said substrate at locations adjacent to said carbonyl compound, wherein the halogenated hydrocarbon compound contains at least one halogen selected from the group consisting of chlorine, bromine, and iodine;
   c) means for exposing said sensing element to said excitation light;
   d) means for collecting light emitted by said carbonyl compound;
   e) means for filtering said collected light to remove scattered excitation light and stray light which is collected along with said emitted light;
   f) means for measuring the intensity of said filtered light;
   g) means for exposing said sensing element to a sample environment comprising gaseous oxygen;
   h) means for exposing said sensing element to calibration environments; and,
   i) means for determining oxygen concentration in said sample environment by comparing light intensity measured while the sensing element is exposed to said sample environment to light intensities measured while the sensing element is exposed to said calibration environments.

2. The apparatus of claim 1 wherein said means for producing substantially monochromatic excitation light is comprised of a light source which produces light of numerous wavelengths and an optical filter which passes only light having wavelengths in a narrow band of wavelengths.

3. The apparatus of claim 1 wherein said means for filtering collected light passes only light having wavelengths centered about 460 nanometers.

4. The apparatus of claim 1 wherein each of said means for exposing said sensing element to said excitation light and said means for collecting light comprises a fiber-optic light guide to conduct excitation light to said sensing element and to conduct emitted light away from said sensing element.

5. A sensor for gaseous oxygen comprised of:
   a) a polar substrate having free hydroxyl groups at its surface:
   b) a luminophor compound, which is a conjugated aromatic carbonyl compound, deposited on the surface of said substrate wherein said luminophore compound is N-methylacridone;
   c) a halogenated hydrocarbon compound deposited on the surface of said substrate at locations adjacent to said carbonyl compound, wherein the halogenated hydrocarbon compound contains at least one halogen selected from the group consisting of chlorine, bromine, and iodine;
   d) at least one fiber-optic light guide for conducting excitation light to said substrate; and,
   e) at least one fiber-optic light guide for conducting light emitted by said carbonyl compound away from said substrate.

6. The sensor of claim 5 wherein said substrate is chosen from the group consisting of alpha alumina, etched glass beads, strongly acidic ion-exchange resins, and activated silica gel.

7. The sensor of claim 5 wherein said halogenated hydrocarbon compound is chosen from the group consisting of dichloromethane, diiodonmethane, methyl iodide, 1-bromo-2-chloroethane, 1-bromo-1-chloroethane, iodoform, 1,1-dibromoethane, and methylene chloride.

8. The sensor of claim 5 wherein each molecule of said halogenated hydrocarbon compound contains no more than four carbon atoms.

9. The sensor of claim 5 wherein said halogenated hydrocarbon compound is methylene chloride.

10. The sensor of claim 5 wherein said substrate, with said luminophor and halogenated hydrocarbon compounds located thereon, is enclosed within a selectively permeable membrane which prevents interfering substances from contacting said luminophor.

11. The sensor of claim 5 wherein said substrate is comprised of particles of activated silica gel and said particles are contained within a gas permeable membrane.

12. The sensor of claim 11 wherein said particles range in size from a mean particle diameter of about 10 microns to about 100 microns.

13. A method for detecting the presence of gaseous oxygen and measuring the amount present comprising:
a) exciting a luminophor compound with substantially monochromatic light having wavelengths effective for absorption by said luminophor, wherein the luminophor is located on a polar substrate having free hydroxyl groups, wherein a halogenated hydrocarbon compound containing at least one halogen selected from the group consisting of chlorine, bromine, and iodine is located on the substrate at locations adjacent to the luminophor, and wherein the luminophor is N-methylacridone;
b) collecting light emitted by the luminophor at wavelengths different from those of said excitation light;
c) measuring the intensities of said collected light when said luminophor is located in a calibration environment comprising gaseous oxygen of at least two different concentrations, thus providing at least two intensity measurements;
d) measuring the intensity of said collected light when said luminophor is located in a sample environment comprising gaseous oxygen; and,
e) determining the oxygen concentration of said sample environment by comparing said sample environment intensity to said calibration environment intensities.

14. The method of claim 13 wherein wavelengths of said substantially monochromatic excitation light are centered about 400 nanometers.

15. The method of claim 13 wherein the wavelengths of said emitted light are centered about 460 nanometers.

16. The method of claim 13 wherein said halogenated hydrocarbon is methylene chloride.

17. The method of claim 15 wherein said substrate is activated silica gel.

* * * * *